US012778475B2

(12) United States Patent
Robinson-Mosley

(10) Patent No.: US 12,778,475 B2
(45) Date of Patent: Nov. 3, 2026

(54) SYSTEM AND METHOD FOR SPORTS MENTAL HEALTH FITNESS TRACKER

(71) Applicant: The Sports Mental Health & Wellness Playbook Corporation, Atlanta, GA (US)

(72) Inventor: T.M. Robinson-Mosley, Atlanta, GA (US)

(73) Assignee: The Sports Mental Health & Wellness Playbook Corporation

( * ) Notice: Subject to any disclaimer, the term of this patent is extended or adjusted under 35 U.S.C. 154(b) by 0 days.

(21) Appl. No.: 19/000,782

(22) Filed: Dec. 24, 2024

(65) Prior Publication Data

US 2025/0204826 A1 Jun. 26, 2025

Related U.S. Application Data

(60) Provisional application No. 63/614,675, filed on Dec. 26, 2023.

(51) Int. Cl.
*A61B 5/16* (2006.01)
*G16H 10/20* (2018.01)

(52) U.S. Cl.
CPC ............ *A61B 5/165* (2013.01); *G16H 10/20* (2018.01)

(58) Field of Classification Search
None
See application file for complete search history.

(56) References Cited

U.S. PATENT DOCUMENTS

| | | | |
|---|---|---|---|
| 9,728,101 | B2 | 8/2017 | Osborn |
| 10,614,724 | B2 | 4/2020 | Catani et al. |
| 11,013,449 | B2 | 5/2021 | Sriram |
| 11,430,567 | B2 | 8/2022 | Johnstone et al. |
| 11,529,074 | B2 | 12/2022 | Vaterlaus |

(Continued)

FOREIGN PATENT DOCUMENTS

| | | | |
|---|---|---|---|
| CN | 107405072 | B | 12/2021 |
| EP | 3262548 | A1 | 1/2018 |
| WO | 2019137538 | A1 | 7/2019 |

OTHER PUBLICATIONS

Cutler Wellness Programs; “Athlete Mental Health LINK”, available at: https://www.athletementalhealthlink.com, retrieved in Jul. 2025, pp. 7.

(Continued)

*Primary Examiner* — Sana Sahand
(74) *Attorney, Agent, or Firm* — Gearhart Law LLC

(57) ABSTRACT

A system and method for sports mental health fitness tracker. The system and method determines the impact of mental well-being on sports performance. The system includes a questionnaire component, interpreting component, aggregating component, and first and second display screens. The method includes obtaining information regarding the habits, behaviors, stress and overall well-being of an athlete by the questionnaire component. The information is processed by the interpreting and aggregating components to transmit electrical signals to the first and second display screens. The first display screens provide information regarding the mental well-being of individual athletes. The second display screen provides information regarding the mental well-being of more than one athlete as a group.

20 Claims, 10 Drawing Sheets

(56) References Cited

U.S. PATENT DOCUMENTS

| | | | | |
|---|---|---|---|---|
| 11,723,568 | B2 | 8/2023 | Jernigan | |
| 2002/0007105 | A1 | 1/2002 | Prabhu et al. | |
| 2006/0150989 | A1* | 7/2006 | Migaly | A61B 5/165 128/898 |
| 2009/0069641 | A1* | 3/2009 | Cho | A61B 5/165 600/300 |
| 2011/0301433 | A1* | 12/2011 | Sadowsky | G16H 20/70 600/300 |
| 2015/0120205 | A1* | 4/2015 | Jeon | A61B 5/015 702/19 |
| 2016/0074707 | A1 | 3/2016 | Thorpe et al. | |
| 2017/0103668 | A1* | 4/2017 | Chatterjee | A61B 5/14551 |
| 2018/0276345 | A1 | 9/2018 | Von Cavallar et al. | |
| 2018/0303396 | A1* | 10/2018 | Wild | G16H 10/60 |
| 2019/0088159 | A1 | 3/2019 | Minturn | |

OTHER PUBLICATIONS

Mindbody, Inc.,The Zone Sports & Fitness, on Google Play Store available at: https://play.google.com/store/apps/details?id=com.fitnessmobileapps.redzonesportsfitness39480&hl=en_US, last Updated on Apr. 29, 2025, retrieved on Jun. 9, 2025, pp. 3.

U.S. Appl. No. 63/614,675, filed Dec. 26, 2023, pp. 34.

* cited by examiner

SYSTEM AND METHOD FOR SPORTS MENTAL HEALTH FITNESS TRACKER

CROSS-REFERENCE TO RELATED APPLICATIONS

This application is a U.S. Non-Provisional Utility Patent Application entitled, "SYSTEM AND METHOD FOR SPORTS MENTAL HEALTH FITNESS TRACKER" that claims priority to U.S. Provisional Patent Application No. 63/614,675, filed on Dec. 26, 2023 entitled, "SYSTEM AND METHOD FOR SPORTS MENTAL HEALTH FITNESS TRACKER" the contents of which are hereby fully incorporated by reference.

FIELD OF THE EMBODIMENTS

The field of the invention and its embodiments relate to a system and method for determining the impact of mental well-being on sports performance.

BACKGROUND OF THE EMBODIMENTS

Approximately 40% of elite athletes battle depression, but traditional athletic solutions neglect the impact of mental health and overall well-being on sports performance. Traditional athletic performance solutions heavily focus on improving the skill development and physical health of athletes without recognizing the impact of mental health and overall well-being on performance.

Skill development and the physical health of athletes are factors in sports performance. However, mental health and overall well-being may be equally and possibly more significant factors. If mental health and overall well-being are not taken into account when evaluating the present as well as future performance of an athlete, then the findings and conclusions of the evaluation may be incomplete and/or erroneous.

Incomplete and/or erroneous evaluations of the present and future performance of athletes may have negative consequences in athletics. Such evaluations may be detrimental to athletes since they can lead to less than optimal coaching of the athlete. Consequently, the athlete may not reach the full potential provided by their natural abilities. This may cause the athlete to become discouraged with their athletic pursuits and possibly cause negative psychological consequences which are significant. In extreme cases, the athlete may become so discouraged that they stop pursuing athletics entirely. This consequence would be very unfortunate particularly in the case of a gifted athlete who, with proper coaching, could flourish in their athletic pursuits.

Further, incomplete and/or erroneous evaluations of the present and future performance of athletes can have significant negative consequences in sports from an economic standpoint. The performance of athletes, both at the college and professional levels, is a major factor in the entertainment value and popularity of individual athletes as well as teams. Athletes that perform at a high level have an increased likelihood of economic rewards individually.

Regarding teams, they are of course a collection of individual athletes. Athletic success of individual athletes generally leads to success of the team and associated economic rewards. Accordingly, assembling a team of individual athletes that have high present and future performance generally results in economic benefits for the team. Maximizing the performance of athletes is generally impeded by incomplete or erroneous evaluations of the present and future performance of the athletes on the team.

SUMMARY OF THE EMBODIMENTS

The present invention and its embodiments relate to a system and method for a sports mental health fitness tracker. The system and method provides information on the impact of mental well-being on the sports performance of an individual athlete. The system and method also provides information on the impact of mental well-being on the sports performance of a group of athletes, such as a sports team. Information on the mental well-being of an individual athlete as well as a team typically helps coaches understand the reasons for the current performance of the athlete and team.

The system and method for a sports mental health fitness tracker provides data and/or information on the impact of mental well-being on an individual athlete and/or a team by measuring one or more factors including, but not limited to, stress, well-being, and/or bounce back (i.e., resilience). This unlocks personal insights that help athletes make data-driven decisions that best support performance and may provide peak performance. It has been found that peak athletic performance includes a balance of physical and mental health.

In an embodiment, the system and method may be referred to as The Playbook™ which was built on the knowledge that mental health and overall well-being have just as much of an impact on performance as physical health and skill. Typically, player safety and well-being are a priority. The system implements an application on a graphical user interface (GUI) of a display of an electronic device and brings a new approach to traditional athletic performance solutions by measuring stress, well-being, and bounce back (i.e. resilience) which offers athletes data-driven insights to improve performance while presenting their teams with increased competitive advantages.

Through daily tracking and real-time analysis, the system may give organizations visibility into how their teams are doing beyond the game. By tracking over time and prompting a team to engage daily, a user may recognize upticks in team and/or individual performance and prepare for immediate action as soon as an athlete enters the Red Zone, meaning they have dipped into an unhealthy range.

In an embodiment, the system is configured to helps a user care for one or more people before a problem becomes a crisis. The information regarding the mental well-being of an individual athlete provides for the system and method to be a personalized digital wellness and performance coach. The system and method uses responses to brief questionnaires to provide insights into habits, behaviors, stress and overall well-being. The system and method serves practical psychological tools and strategies, recommendations, and coaching that help leverage strengths, manage stress, and maximize performance.

In an embodiment, the system and method for the sports mental health fitness tracker is configured with two users in mind: The Athlete & The Administrator. For the athlete users, the app quantifies mental health status through gamified assessments, providing an overall score like a batting average. The app tracks stress, well-being, and resilience over time, offering practical psychological tools and strategies to maximize performance. The information regarding the mental well-being of a team may be referred to as team analytics which may illustrate improvement and/or impairment of the team. The system and method monitors one or more metrics of the team, allowing coaches to understand when athletes are within a healthy range and to send alerts when an athlete needs immediate attention. This offers real-time opportunities for support and risk mitigation.

For the administrator users, they access a web-based dashboard for a team-wide mental health overview. They can drill down into individual athlete profiles and receive HIPAA compliant notifications when an athlete needs immediate attention. Daily tracking enables real-time trend analysis, empowering proactive interventions rather than reactive crisis responses. When an athlete's routine assessments indicate they have fallen into an unhealthy range, such as The Red Zone, they are immediately directed to tailored mental health resources to access support inside and outside of the team.

In an embodiment, the admin is alerted simultaneously that a player has entered the Red Zone, prompting them to initiate a Red Zone Action Plan—a step-by-step rapid risk assessment to help determine next steps and connect athletes to the resources they need. The system's Red Zone Action Plan ensures that one or more players are not left alone in the moments when they need help the most.

The system and method facilitates the development of a game plan to operate at optimal team performance. High impact executive coaching is also facilitated. The system and method additionally facilitates wellness and performance programming based on the needs of the organization and individual. 1:1 coaching and group focused huddles are facilitated by the system and method. Personalized progress tracking and team-wide workshops are provided by the system and method. The peak performance that may be provided by the system and method gives the associated team a competitive advantage.

The system and method aims to track, treat, and improve overall well-being and performance for athletes and individuals that are operating at the highest level. Providing information regarding the mental well-being of individual athletes provides practical tools and strategies over time, and personal insight. This empowers the athletes to leverage strengths, manage stress, and perform at their best.

Providing information regarding the mental well-being of a team offers support staff a team-wide mental health overview. This is like a grade point average (GPA) derived from the self-reported assessments of individual athletes. Providing information regarding the mental well-being of a team helps track progress and identify when an athlete needs support. The information regarding the mental well-being of a team may be presented on an administrative dashboard which may provide a team-wide mental health overview.

The system and method may be used in high-performance industries that have no direct connection to athletics or sports. In such industries, the system and method is tailored to meet the unique needs and stressors of the respective industry. The system and method may also be applied to the business-to-consumer (B2C) market for high-performance individuals. Similar to leveraging wearable technologies, the system and method may empower users to monitor and enhance their overall performance through the lens of mental health. Digital embodiments of the system and method will enable the expansion of the customer base for the system and method to customers for whom the premium based system and method may be too costly.

DESCRIPTION OF THE PREFERRED EMBODIMENTS

Figure 1:
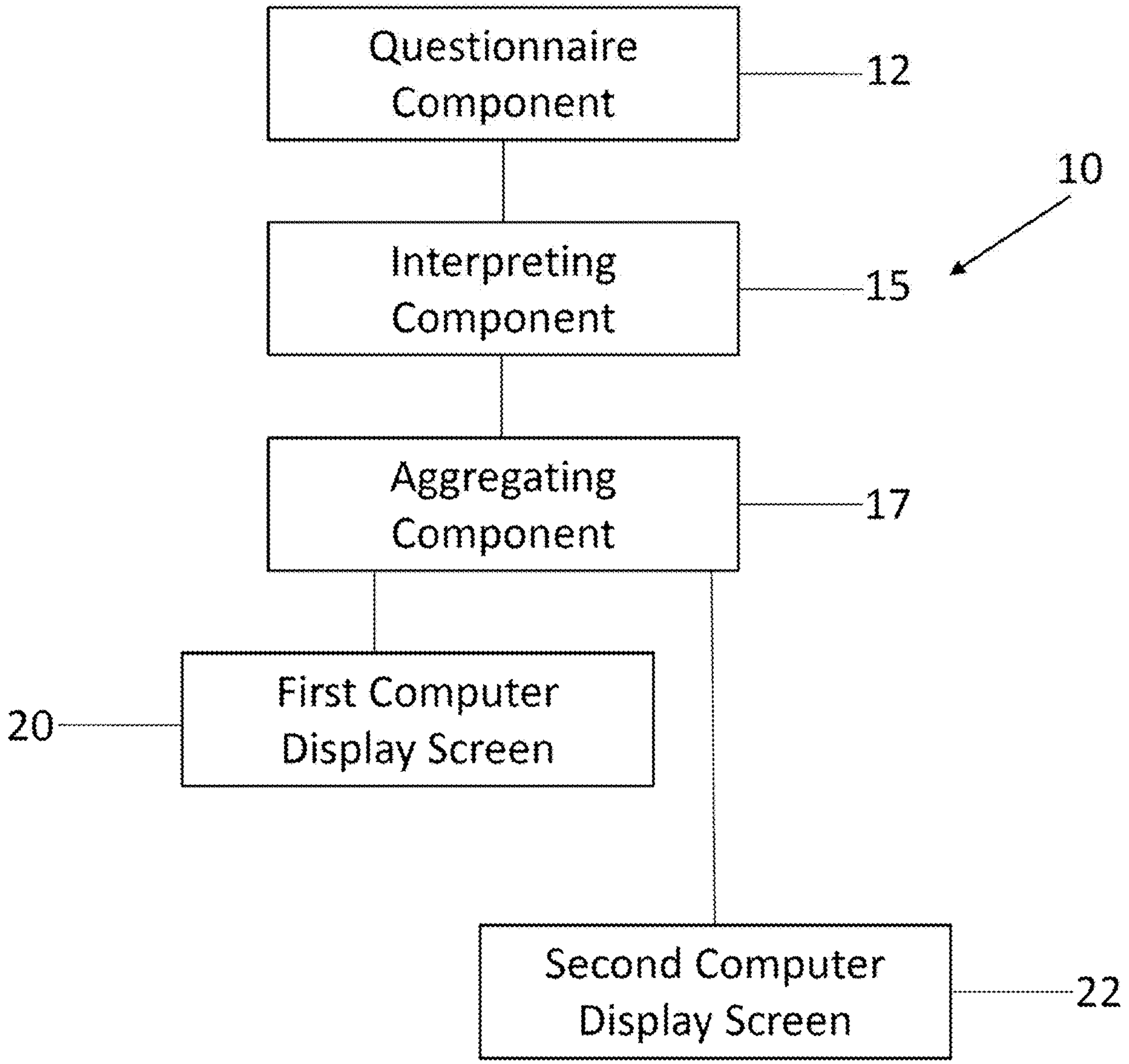
FIG. 1 depicts a high-level block diagram illustrating the system for sports mental health fitness, the components for the system being shown as blocks according to at least some embodiments described herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3-5 ng, and 4-5 ng.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

FIG. 1 illustrates an embodiment of the system for sports mental health fitness tracker 10. The system 10 includes a questionnaire component 12 for obtaining information regarding the habits, behaviors, stress and overall well-being of one or more athletes. The questionnaire component 12 changes the information to one or more electrical signals indicating the habits, behaviors, stress and overall well-being of the one or more athletes.

The system 10 also includes an interpreting component 15 connected to the questionnaire component 12. The interpreting component 15 receives the one or more electrical signals indicating the habits, behaviors, stress and overall well-being of the one or more athletes from the questionnaire component 12 and determines the psychological states of the one or more athletes. Additionally, the interpreting component 15 changes the determination of the psychological states into one or more state electrical signals in which each state electrical signal indicates the psychological state of an individual athlete.

The system 10 additionally includes an aggregating component 17 for receiving the one or more of the state electrical signals indicating the psychological states of the one or more athletes. If there is more than one of the state electrical signals, then the aggregating component 17 processes the state electrical signals to generate a group electrical signal indicating the psychological state of the athletes as a group. The group electrical signal may indicate additional information regarding the athletes as a group as provided by the aggregating component 17. The aggregating component 17 transforms each state electrical signal to a respective first electrical signal. The aggregating component 17 transforms the group electrical signal into a second electrical signal.

The system 10 further includes a first display screen 20 of an electronic device such as a computer, a smart device, a tablet, and/or a processor, connected to the aggregating component 17. The first display screen 20 receives the first electrical signal from the aggregating component 17 indicating the psychological state of one of the athletes. The first display screen 20 transforms the first electrical signal received from the aggregating component 17 to a view indicating the psychological state of the individual athlete corresponding to the signal on the first display screen. The first display screen 20 may be provided by the display screen of a smart phone or similar device.

The system 10 further includes a second display screen 22 connected to the aggregating component 17. The second display screen 22 receives the second electrical signal from the aggregating component 17. The second display screen 22 transforms the second electrical signal from the aggregating component 17 to a view indicating the psychological state of the more than one athlete as a group on the second display screen 22. The second display screen 22 may be provided by the display screen of a laptop computer, tablet computer or similar device.

Figure 2:
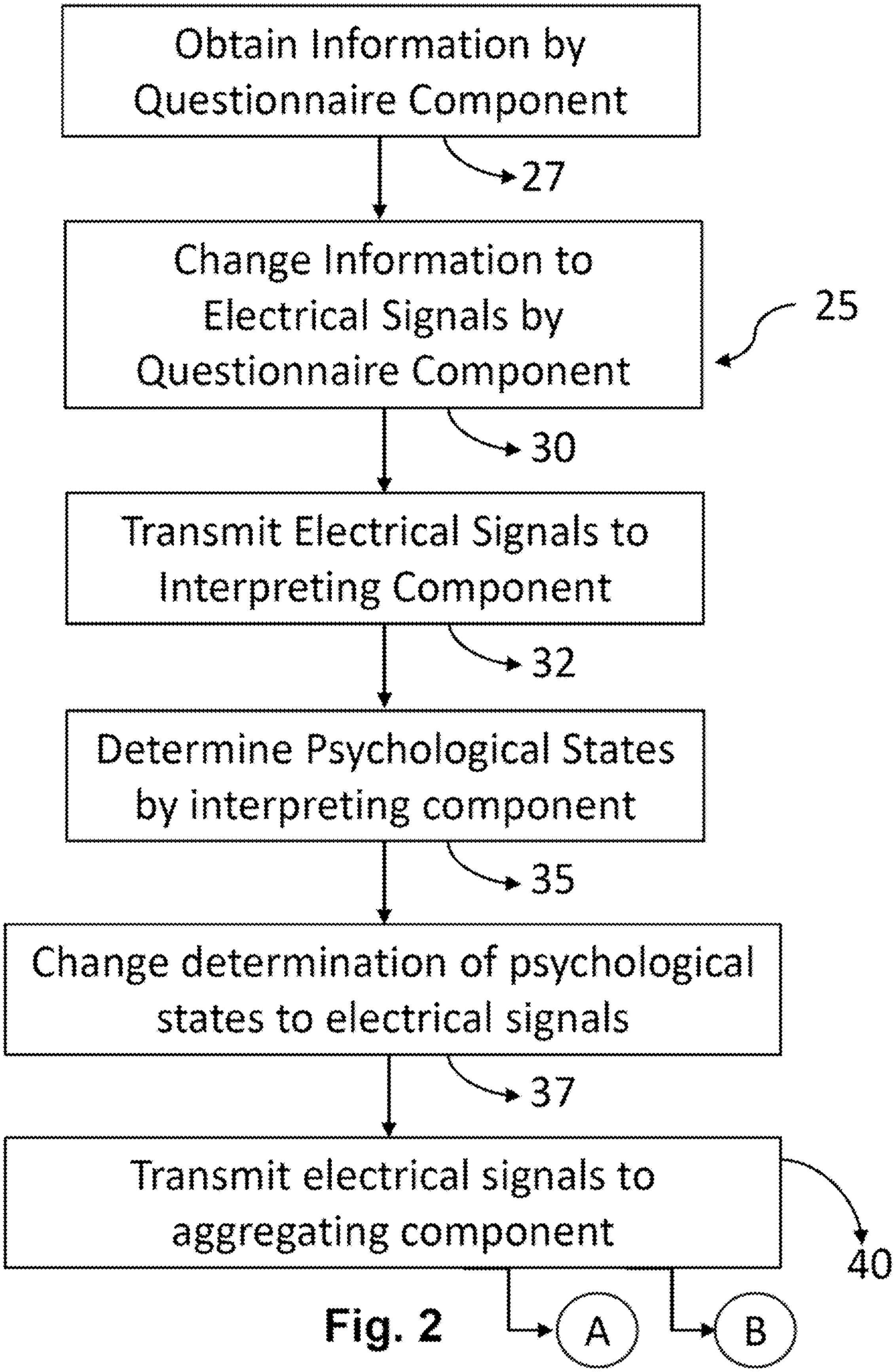
FIG. 2 depicts a flowchart showing a method for operating the system of FIG. 1, the flowchart identifying the use of the components of FIG. 1 in the method according to at least some embodiments described herein.

FIG. 2 depicts a flowchart showing an example method for operating the system of FIG. 1, the flowchart identifies the use of the components of FIG. 1 in the method. The system 10 is operated according to the example method 25 in which information regarding the habits, behaviors, stress and overall well-being of one or more athletes is obtained 27 by the questionnaire component 12. Next, the information indicating the habits, behaviors, stress and overall well-being of the one or more athletes is changed 30 to one or more electrical signals corresponding to each athlete by the questionnaire component 12. Then, the electrical signals indicating the habits, behaviors, stress and overall well-being of the one or more athletes are transmitted 32 to the interpreting component 15 connected to the questionnaire component 12.

Next, the psychological states of the one or more athletes are determined 35 by the interpreting component 15. The interpreting component 15 changes 37 the determinations 35 of the psychological states to state electrical signals indicating the psychological states of corresponding ones of the individual athletes. The one or more state electrical signals are transmitted 40 from the interpreting component 15 to the aggregating component 17. The aggregating component 17 transforms each state electrical signal to a respective first electrical signal.

Figure 3:
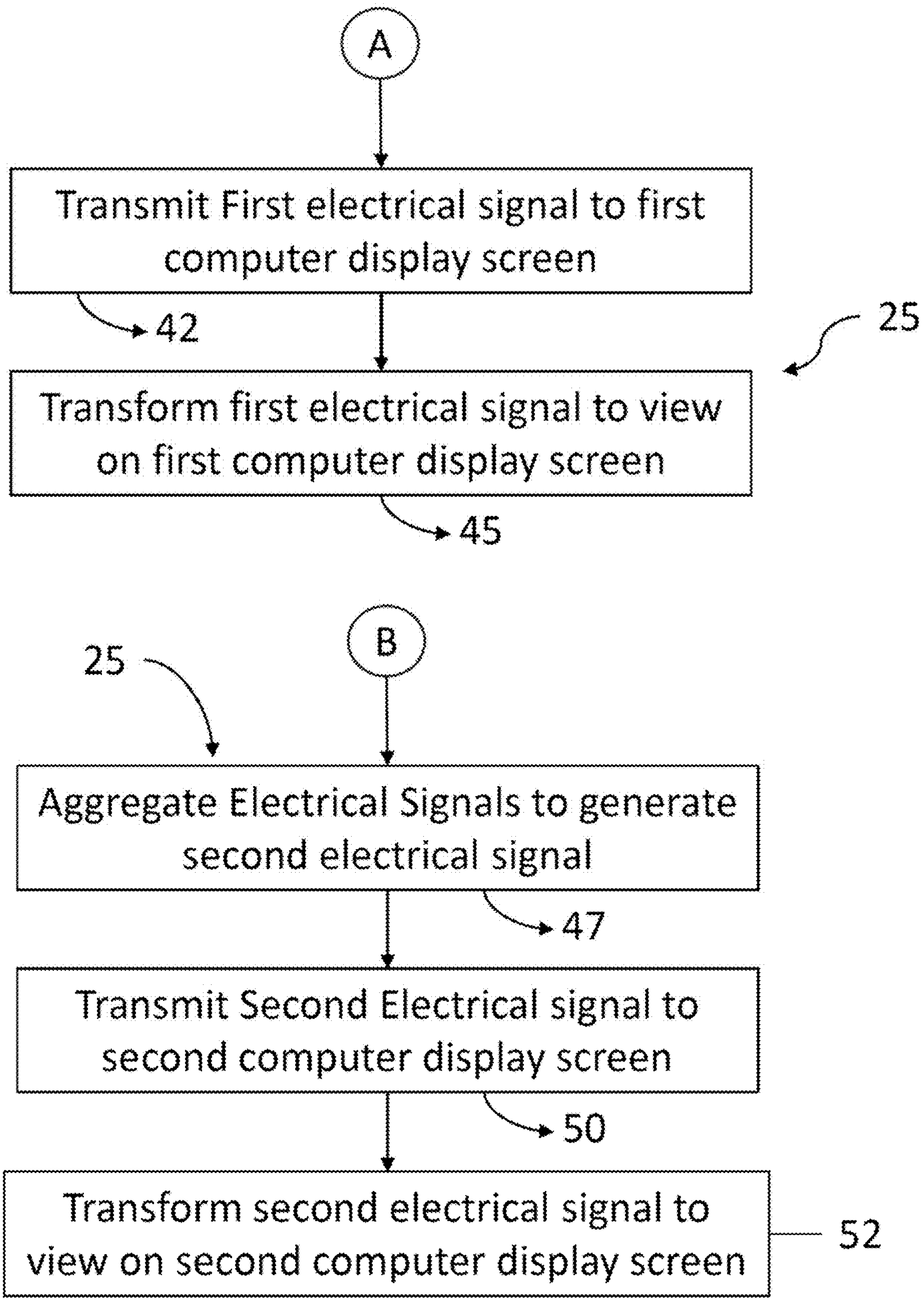
FIG. 3 depicts a flowchart further illustrating the method from FIG. 2, in accordance with some embodiments.

FIG. 3 depicts a flowchart further illustrating the method from FIG. 2, in which each of the first electrical signals is transmitted 42 from the aggregating component 17 to a respective first display screen 20. The first display screen 20 transforms 45 the first electrical signal to a view on the first display screen.

Each of the first display screens 20 shows a view containing information relating to a single athlete. Accordingly, there is a first display screen 20 corresponding to each individual athlete. Each of the first display screens 20 may show well-being metrics for a corresponding individual athlete. For example, the system generates an overall well-being score for the athlete, which is calculated on a scale from 0 to 100. This score is accompanied by a colored flag that visually represents the athlete's well-being, with the flag's color indicating the athlete's current state, such as green for healthy, yellow for caution, or red for needing attention. The well-being score is derived from multiple input data points, and the system tracks the number of inputs used in the calculation. Additionally, the system records the range of dates during which these inputs were collected. To provide a clearer understanding of the athlete's well-being over time, a graph is generated that displays the overall well-being score across different dates, with each point on the graph representing an individual input and the corresponding date it was collected. This visual tool helps track changes and trends in the athlete's mental health, offering valuable insights for further analysis and action.

The Playbook App Features Overview instructs the individual athlete to practice better and explore all of the individual athlete's focused practices. The Playbook App Features Overview includes access to gamified microlearning processors, customized mental health and wellness exercises, and helpful tips and toolkits. The Playbook App Features Overview provides for the first display screen 20 to show a Wellness 101: Self Care Game Plan. The display screen 20 may explain that Self Care includes activities that are done deliberately in order to take care of the emotional, mental, and/or physical health of the individual athlete. Self Care is the ultimate tool for managing stress, combating emotional disregulation, and improving mood. The Playbook App Features Overview instructs the individual athlete to practice habit stacking, and a self care game plan. Also, the Playbook App Features Overview provides the individual athlete with focused practices, customized mental health and wellness exercises, and helpful tips and toolkits.

Player Access is provided to practice gamified microlearning processors. The display screen 20 may show a practice processor directed to a self care game plan. The self care game plan may include deliberate, structured activities to take care of the athlete's emotional, mental, and physical health. A different practice processor may be directed to practicing better by exploring all of the athlete's focused practices, customized mental health and wellness exercises, and helpful tips and toolkits. Player Access also provides the Wellness 101: Self Care Game Plan which may also be shown on the display screen 20. Self Care includes activities that are done deliberately in order to take care of the emotional, mental, and physical health of the individual athlete. Self Care is the ultimate tool for managing stress, combating emotional disregulation, and improving mood.

The Player Access also enables an individual to join a locker room for self care, habit stacking, and playbook performance on the display screen 20. The Player Access further provides for Video and Chat between individuals in different locker rooms using the display screen 20. The Playbook Practice Better includes customized messages on the display screen 20 for the athlete such as "Hey There, [athlete's name]! . . . . How are you feeling today?" Following this question are several emoji's indicating different emotional states from happy to sad. The day and date are also shown on the display screen 20.

If there is more than one of the first electrical signals, then the aggregating component 17 processes the first electrical signals to generate 47 a group electrical signal indicating the psychological state of the athletes as a group. The group electrical signal may indicate additional information regarding the athletes as a group as provided by the aggregating component 17. The aggregating component 17 transforms the group electrical signal into a second electrical signal.

The second electrical signal is transmitted 50 from the aggregating component 17 to the second display screen 22. The second electrical signal from the aggregating component 17 is transformed 52 to a view indicating the psychological state of the more than one athlete as a group by the second display screen 22. The view presented by the second display screen 22 may include various types of information relating to the athletes as a group. It identifies players needing immediate attention, instructing that a wellness check be performed on such players within 24 hours, with these players being associated with a red flag. It also identifies players who are close to receiving a red flag, associating them with a yellow flag, and those who are close to receiving a yellow flag, associating them with a green flag. Additionally, the display may provide an Optimal Performance illustration that shows a distribution of green and yellow circles, a Team Playbook Performance score associated with a green flag, and a Team Well-Being score associated with a red flag.

In a further alternative embodiment, the system 10 may include a single display screen 22 that presents a view indicating the psychological state of more than one athlete as a group. Such a single display screen 22 may be provided by a laptop computer, tablet computer or similar device. Such an alternative embodiment would not include the first display screens 20.

In a further alternative embodiment, the system 10 may include multiple computer screens 20 where each screen presents views indicating the psychological state of a single athlete. Such computer screens 20 may be provided by the display screen of a smart phone or similar device. Such an alternative embodiment would not include the second display screen 22.

A system for tracking athlete mental health fitness is may include one or more interrelated components that enable a comprehensive assessment and management of individual and group psychological states. The system includes a questionnaire component designed to obtain detailed information about habits, behaviors, stress levels, and overall well-being from athletes. This component uses a digital interface, such as a mobile app or web platform, to allow athletes to input data through multiple-choice questions, sliding scales, and open-ended text fields. For example, athletes may respond to questions about their sleep patterns, stress sources, and coping strategies. The input data is then converted into electrical signals, which serve as the basis for further analysis.

The processor in the system is responsible for interpreting and processing the data received from the questionnaire component. When the athlete inputs responses regarding their habits, behaviors, stress levels, and overall well-being, these responses are converted into electrical signals. The processor receives these signals and performs a series of operations, including data validation, transformation, and analysis. For example, it may aggregate multiple data points, such as stress levels over the past week, to calculate a single overall well-being score. This score might be calculated based on a weighted average of different categories (e.g., stress, sleep quality, mood), where each input is assigned, a specific value based on its importance.

The processor also performs comparisons to identify trends in the athlete's mental state over time. For instance, it could track changes in well-being scores over several weeks or months, flagging significant deviations or patterns. If a decline in well-being is detected, such as a consistent drop in mood scores, the processor could trigger an alert indicating that further attention is needed. Once the processing is complete, the processor transmits the results to output devices. For instance, it sends the calculated well-being score to a display screen that shows the score as a numerical value, along with a colored flag that visually indicates the athlete's state (e.g., green for healthy, red for requiring intervention). The processor also sends the aggregated group data to a secondary display, where it may show a visual representation of the team's overall mental health, including performance metrics and a distribution of well-being scores for all athletes. The processor is thus central to managing data flow, performing calculations, and ensuring that the system's outputs reflect accurate psychological assessments.

An interpreting component processes the data received from the questionnaire component. It employs advanced algorithms to analyze the inputs and determine psychological states such as anxiety, motivation, or burnout. The interpreting component translates these psychological states into state electrical signals, each uniquely corresponding to an athlete's mental and emotional condition. For instance, an athlete reporting low energy and high stress may be classified as experiencing burnout, with this state flagged for additional attention.

The system also includes an aggregating component that synthesizes individual psychological state data into a cohesive group-level analysis. This component processes state electrical signals to create a group electrical signal that reflects the psychological state of the team as a whole. It is capable of identifying patterns, such as an overall decrease in team morale, and transforming the data into actionable insights. For example, the aggregating component may highlight that 70% of athletes have reported high stress levels over the past week, signaling the need for intervention. This processed data is converted into first and second electrical signals representing individual and group states, respectively.

Two display screens present the analyzed data. The first display screen, designed for detailed individual analysis, provides personalized views of an athlete's mental health metrics. These include an overall well-being score, color-coded flags (e.g., green for healthy, yellow for caution, and red for concern), and graphical trends that track changes over time. For instance, a coach can see that a particular athlete's stress score has risen steadily over the past month. Additionally, the first screen offers suggestions for self-care activities, such as breathing exercises or mindfulness practices, tailored to the athlete's specific needs.

The second display screen focuses on team-level insights and trends. It presents aggregated metrics, such as the team's optimal performance distribution, a collective well-being score, and a graphical representation of members requiring wellness checks. For example, the screen may display a team playbook performance score indicating areas of strength and weakness, helping coaches adjust training plans to address challenges.

As noted above, the system for tracking athlete mental health and performance incorporates several hardware components to collect, process, analyze, and display data at both individual and team levels. Athletes begin by interacting with a digital interface, such as a mobile app, web platform, or a dedicated display screen, to input detailed information about their habits, behaviors, stress levels, and overall well-being. This data is gathered through multiple-choice questions, sliding scales, and open-ended text fields, focusing on areas like sleep patterns and sources of stress. The inputs are converted into first electrical signals, which serve as the foundation for subsequent processing.

The interpreting component receives these first electrical signals and applies advanced algorithms to analyze the data. It determines psychological states, such as anxiety, motivation, or burnout, and translates them into state electrical signals that uniquely correspond to each athlete's mental and emotional condition. For example, an athlete reporting low energy and high stress might be classified as experiencing burnout, with their state flagged for immediate attention. These individual state signals are then processed by the system's processor, which validates the data and transforms it into actionable metrics, such as well-being scores calculated using a weighted average of inputs like stress and sleep quality. The processor also identifies trends over time by comparing scores across weeks or months, triggering alerts if significant deviations or declines are detected. These individual metrics are sent to the first display screen, where personalized insights, including well-being scores, graphical trends, and tailored self-care recommendations, are provided for each athlete.

The aggregating component synthesizes individual state signals into a cohesive group-level analysis. This component processes the state signals to generate a group electrical signal that reflects the collective psychological state of the team. The aggregation involves analyzing patterns in individual data, identifying trends such as an overall decline in team morale or a high percentage of athletes reporting elevated stress levels. For example, if 70% of athletes report high stress, the aggregating component highlights this pattern as a significant issue requiring intervention. The group electrical signal is then transformed into a second electrical signal, which is transmitted to the second display screen. This display visualizes aggregated team data, including collective well-being scores, performance distributions, and flagged athletes who need wellness checks. Athletes are categorized using a color-coded flag system: red for those requiring immediate attention, yellow for those at risk, and green for those performing optimally. Additional metrics, such as the Team Playbook Performance score and the Team Well-Being score, offer insights into areas of strength and weakness, guiding coaches in making informed decisions.

In alternative configurations, the system can feature a single display screen showing team-level metrics or multiple screens dedicated to individual data, depending on the specific requirements. This comprehensive system integrates individual and group-level analyses, empowering coaches and athletes with real-time, actionable insights to enhance both mental health and performance outcomes.

The system incorporates several advanced features to enhance usability and effectiveness. The questionnaire component includes real-time feedback, allowing athletes to update their inputs dynamically throughout the day. This ensures that the system captures fluctuations in mental health as they occur. Additionally, the aggregating component employs machine learning algorithms to predict future psychological states, enabling proactive interventions. For instance, if the system identifies a trend of declining sleep quality across the team, it may recommend changes to practice schedules or wellness workshops to address the issue.

The system also integrates gamified elements to engage users. The first display screen includes a self-care game plan with one or more processors that reward athletes for completing tasks like logging sleep hours or practicing stress-relief techniques. These gamified microlearning processors transform mental health management into an interactive and motivating experience. Meanwhile, the second display screen visualizes team performance using dynamic charts and dashboards, creating a clear and actionable overview for coaches and support staff.

Communication and data sharing are facilitated through a communication interface, which supports video and chat functionalities. This allows athletes to connect with mental health professionals or share self-care tips with teammates. For example, an athlete may use the chat feature to discuss their progress in managing stress or request additional support from a coach.

In an embodiment, the system includes a storage processor that archives historical data, enabling longitudinal analysis of individual and group mental health trends. For example, data from past seasons can be compared to identify recurring challenges, such as increased stress during playoff periods. The system's predictive capabilities, combined with its data management and visualization tools, make it a powerful resource for enhancing athlete mental health and performance.

In an embodiment, the data interpretation algorithm processes inputs from the questionnaire component to assess individual psychological states. This algorithm uses supervised learning techniques, such as Support Vector Machines (SVMs) and/or Random Forests, trained on labeled datasets of athlete mental health metrics. For instance, if an athlete reports difficulty sleeping and elevated stress levels, the algorithm assigns weighted scores to each input and computes a composite score representing their mental health state. The algorithm uses feature extraction methods like principal component analysis (PCA) to reduce noise and identify key patterns, enabling precise categorization into states such as "moderate anxiety" or "burnout."

The group aggregation algorithm synthesizes individual mental health scores into a collective team metric. This algorithm applies weighted averaging to combine individual state signals while accounting for the relative influence of each athlete on team dynamics. For example, team captains or key players might have higher weights due to their leadership roles. Additionally, the algorithm incorporates clustering techniques like K-Means to group athletes with similar mental health patterns, providing insights into subgroups within the team. These clusters are then visualized as dynamic heatmaps, which highlight areas of concern for coaches.

A trend prediction algorithm forecasts future psychological states using time-series analysis. The algorithm employs recurrent neural networks (RNNs), specifically Long Short-Term Memory (LSTM) networks, to model temporal dependencies in mental health data. For example, by analyzing weekly stress levels and sleep quality, the algorithm predicts whether an athlete is at risk of experiencing high burnout in the upcoming month. It adjusts its predictions dynamically using Kalman filters, ensuring real-time updates as new data becomes available.

The actionable insights algorithm converts aggregated data into specific recommendations for athletes and coaches. This algorithm uses decision trees and/or rule-based systems trained on evidence-based mental health practices. For instance, if the team's aggregated stress level exceeds a predefined threshold, the algorithm generates recommendations such as scheduling mindfulness sessions or reducing training intensity. These suggestions are ranked by priority using utility scores derived from past effectiveness data.

The real-time feedback algorithm provides immediate responses to athletes' inputs via the questionnaire component. This algorithm employs natural language processing (NLP) to analyze open-ended text responses, identifying key sentiments and concerns. For example, if an athlete describes feeling "overwhelmed by expectations," the algorithm flags this sentiment as negative and suggests stress-relief strategies. It also updates visualizations and metrics on the user interface in real time using incremental learning models, ensuring that feedback remains responsive to new information.

In an embodiment, the machine learning model evaluation pipeline ensures the accuracy and reliability of all predictive algorithms in the system. This pipeline performs cross-validation to assess model performance, measuring metrics such as precision, recall, and F1 score. It uses ensemble techniques like boosting to combine multiple weak learners into a robust predictive model. For example, if an initial algorithm misclassifies high stress as moderate stress, the pipeline identifies the error and fine-tunes the model using additional training iterations. These algorithms collectively form the backbone of the athlete mental health fitness system, providing precise analyses, actionable insights, and dynamic adaptability.

In an embodiment, in addition to the questionnaire answers being transformed into electrical signals, mental health may be measured by the combination of the questionnaire and one or more sensors configured to measure electrical signals of a user, indicating physiological states. The one or more sensors may include, but no be limited to hardware such as electrocardiogram (ECG) sensors, electroencephalogram (EEG) devices, and galvanic skin response (GSR) sensors may be employed. For example, ECG sensors capture heart rate variability (HRV), which correlates with stress and recovery states. EEG devices monitor brainwave patterns, identifying states like relaxation or focus. GSR sensors measure skin conductivity, providing data on emotional arousal. These devices may use bioelectrical impedance or conductive electrodes to capture real-time electrical activity from the body.

The captured signals are processed using microcontrollers or digital signal processors (DSPs) integrated into the sensor processors. Devices like the Texas Instruments MSP430 or Analog Devices ADSP series are commonly used for signal acquisition and pre-processing. For instance, an MSP430 microcontroller filters noise from raw ECG signals using digital filters and extracts key features such as R-R intervals, which are crucial for determining HRV. Similarly, DSPs perform Fourier transforms on EEG signals to separate and analyze different brainwave frequencies, such as alpha or beta waves.

The aggregation and transformation of individual electrical signals are handled by central processing hardware, such as edge computing devices or embedded systems. Examples include the NVIDIA Jetson Nano or Raspberry Pi 4, which collect processed signals from individual sensors and apply machine learning models for state determination. For instance, after receiving HRV data from ECG sensors and alpha-wave patterns from EEG devices, the edge device computes a composite score to represent the athlete's physiological state, such as "optimal recovery" or "high stress."

To aggregate multiple athletes' signals into group-level metrics, high-performance servers or cloud-based platforms are used. Servers equipped with Intel Xeon processors or cloud systems like Amazon Web Services (AWS) Elastic Compute Cloud (EC2) instances handle large-scale data aggregation. For example, the server collects individual scores from edge devices and applies statistical models or clustering algorithms to identify common patterns, such as a team-level state of "elevated stress" or "high engagement."

Finally, the hardware systems transform individual and group metrics into output signals that indicate the physiological and psychological states. Outputs are generated by hardware interfacing with visualization systems, such as HDMI or DisplayPort interfaces for dashboard displays, or Bluetooth processors for transmitting results to mobile apps. For example, a physiological signal showing elevated stress is visualized as a red alert on a coach's dashboard, while a psychological group signal indicating high motivation is represented as a green bar on a mobile app. Each hardware component plays a role, from signal acquisition to aggregation and transformation, ensuring accurate determination of physiological and psychological states at both individual and group levels.

The transformation process in the sports mental health fitness tracker system is implemented through a series of conversions and calculations that take raw data from the questionnaire component and convert it into meaningful signals that can be displayed and analyzed. Initially, the questionnaire component collects data regarding the habits, behaviors, stress levels, and overall well-being of athletes. This information is then transformed into electrical signals, where each athlete's responses are encoded into data points that correspond to various psychological factors. For example, an athlete's reported stress level might be assigned a numerical value between 0 and 100, with higher values indicating greater stress. Similarly, the overall well-being score could be translated into a specific signal representing the athlete's emotional or mental state based on a scale derived from their answers.

Once the initial signals are generated by the questionnaire, these signals are sent to the interpreting component. Here, the transformation process continues with the psychological state of each athlete being determined based on the input data. For instance, if an athlete reports high stress, low energy, and poor sleep, the interpreting component could process these inputs to classify the athlete as experiencing a "high stress" psychological state. This psychological determination is then transformed into a state electrical signal. Each state electrical signal is essentially a refined representation of the athlete's psychological condition, which might be denoted as "State Signal 1" for a highly stressed athlete and "State Signal 2" for a more relaxed individual.

The aggregating component then receives these state electrical signals from the interpreting component. If multiple athletes are involved, the aggregating component processes the individual state signals into a group electrical signal. For example, if one athlete has a high stress signal and another has moderate stress, the aggregating component could combine these individual signals into a group signal that reflects the overall mental health of the team. This might result in a group electrical signal that represents the team's average stress level, such as a signal that indicates the psychological state of the group as "moderate stress." This group signal is then further transformed into a second electrical signal that encapsulates the collective well-being of the athletes.

Finally, these transformed electrical signals are sent to the display screens. The first display screen, which focuses on individual athletes, receives the first electrical signal and transforms it into a visual representation, such as a colored flag indicating mental health status or a graph showing well-being over time. The second display screen, showing the group's collective state, processes the group electrical signal into a display that shows the team's overall psychological condition, often with additional metrics like flag indicators (e.g., red, yellow, green flags) to indicate who may need immediate attention. Thus, the transformation process in the system takes raw data from athletes and progressively refines it into electrical signals, then into visual representations that are easy to interpret and use for decision-making.

Figure 4:
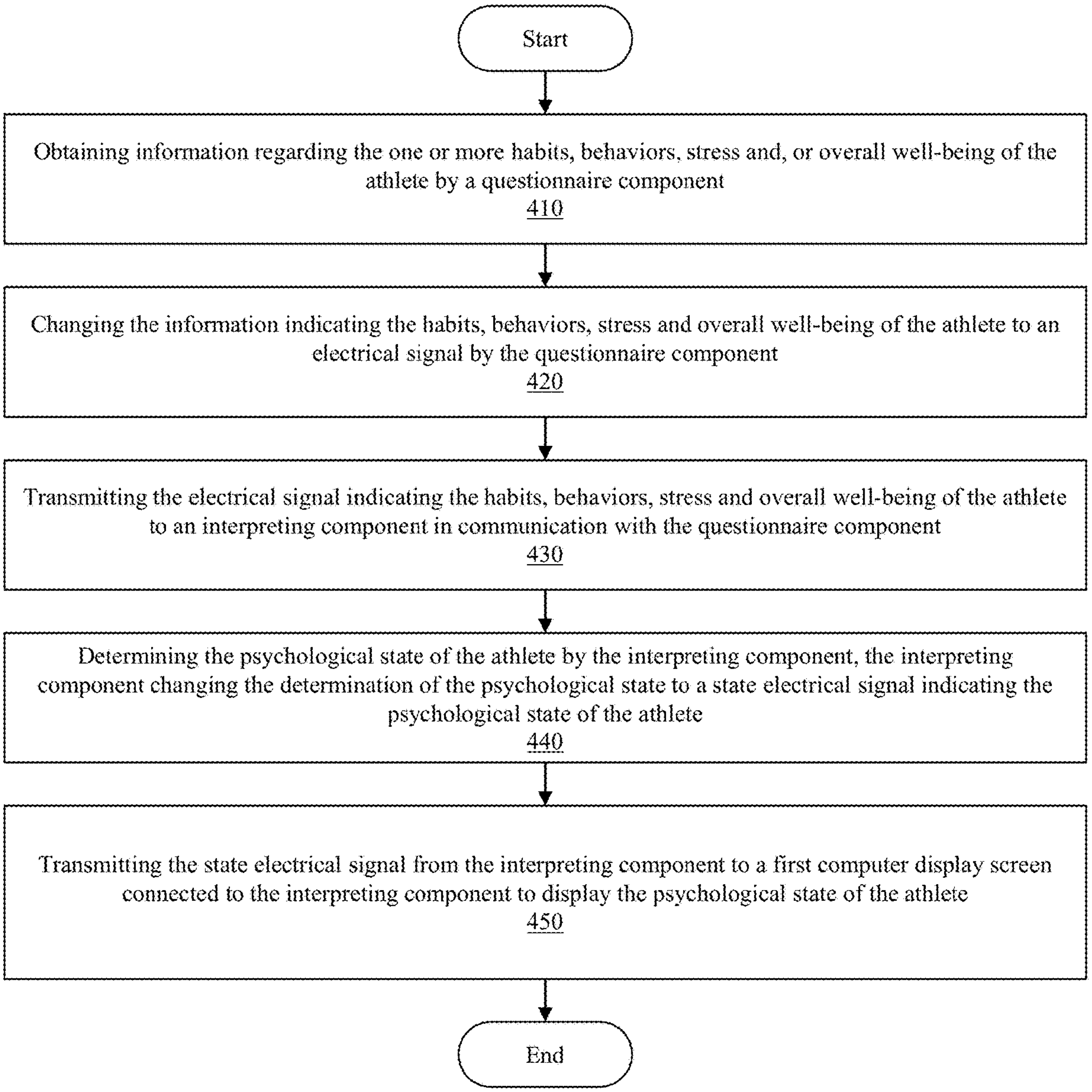
FIG. 4 is a flowchart illustrating a method for measuring the mental health, in accordance with some embodiments.

FIG. 4 is a flowchart that describes an example method for measuring at least mental health, according to some embodiments of the present disclosure. In some embodiments, at 410, the method may include obtaining information regarding the one or more habits, behaviors, stress and, or overall well-being of the athlete by a questionnaire component. At 420, the method may include changing the information indicating the habits, behaviors, stress and overall well-being of the athlete to an electrical signal by the questionnaire component. At 430, the method may include transmitting the electrical signal indicating the habits, behaviors, stress and overall well-being of the athlete to an interpreting component connected to the questionnaire component.

In some embodiments, at 440, the method may include determining the psychological state of the athlete by the interpreting component, the interpreting component changing the determination of the psychological state to a state electrical signal indicating the psychological state of the athlete. At 450, the method may include transmitting the state electrical signal from the interpreting component to a first display screen connected to the interpreting component, the first display screen transforming the state electrical signal from the interpreting component to a view indicating the psychological state of the athlete on the first display screen.

Figure 5A:
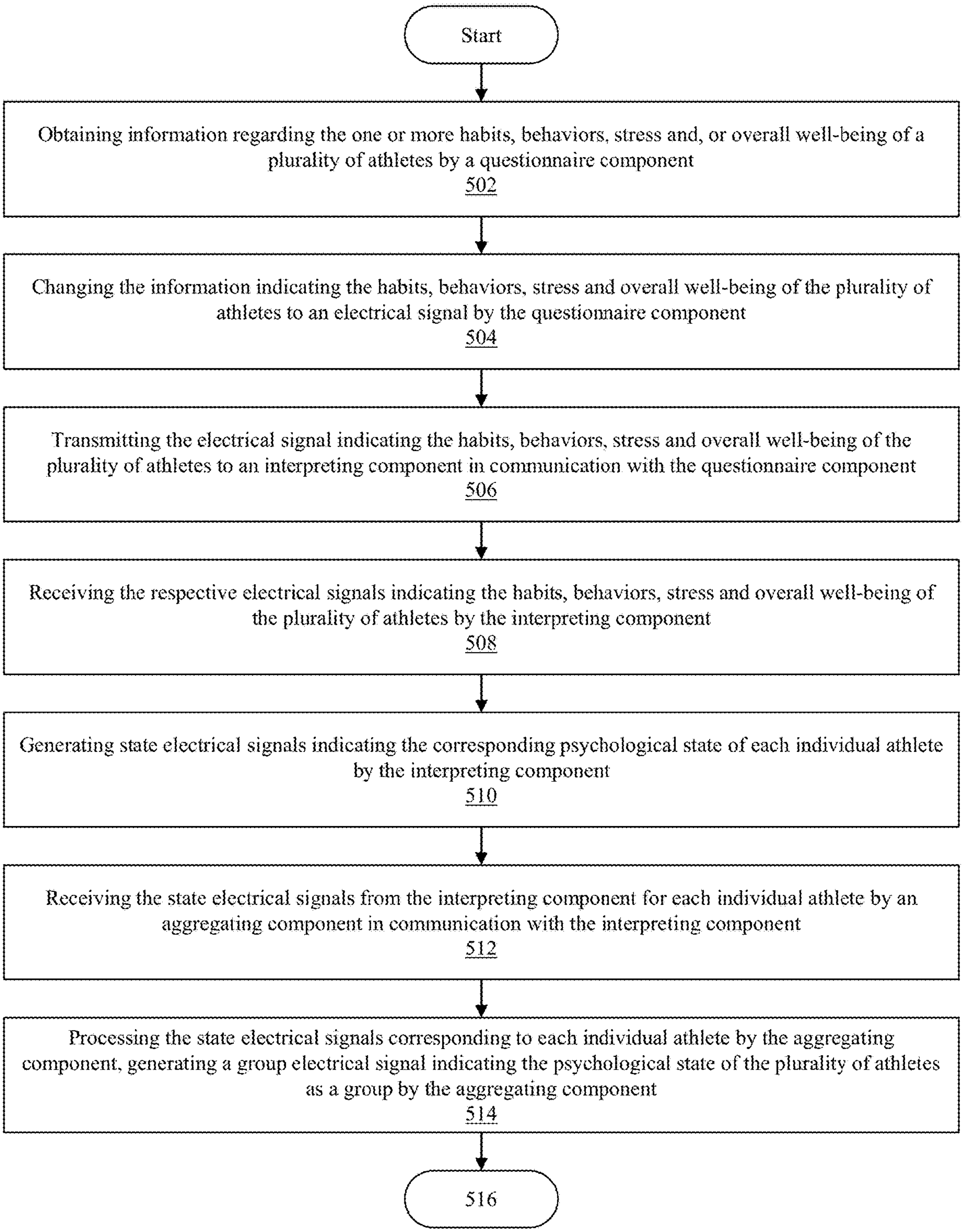
FIG. 5A is an example flowchart illustrating an embodiment of the method for measuring the mental health implementing the system from FIG. 4, in accordance with some embodiments.
Figure 5B:
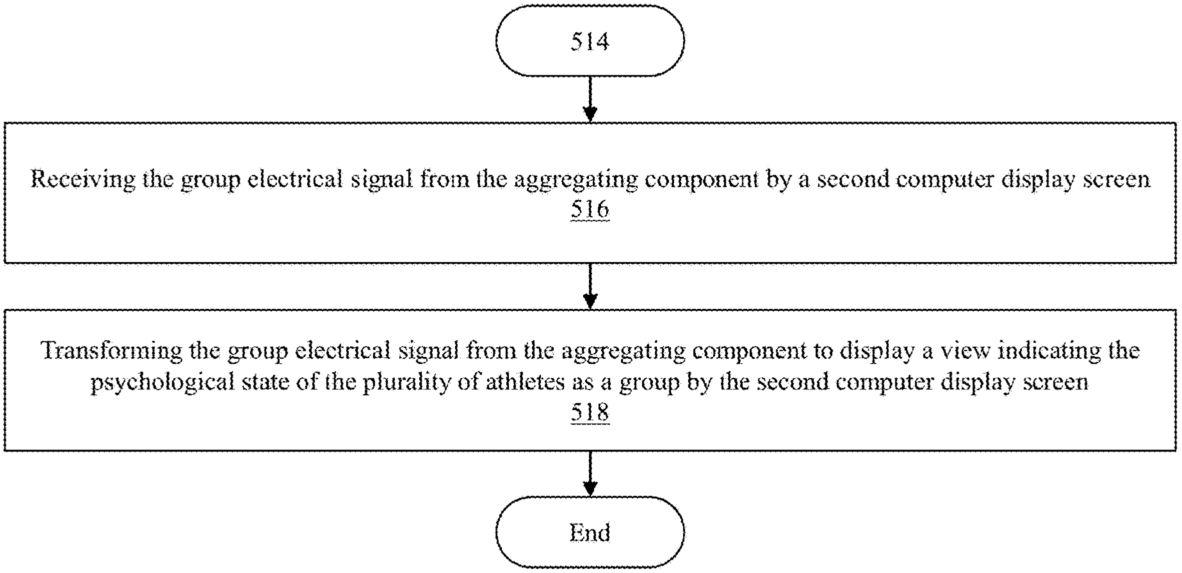
FIG. 5B is a flowchart further illustrating the method from FIG. 5A, in accordance with some embodiments.

FIGS. 5A to 5B are flowcharts that further describe another example method for measuring at least mental health. In some embodiments, the method is configured to measure the mental health and overall well-being of more than one athlete such as a plurality of athletes. At 502, the method may include obtaining information regarding the habits, behaviors, stress and overall well-being of the more than one athlete by the questionnaire component. At 504, the method may include changing the information indicating the habits, behaviors, stress and overall well-being of the more than one athlete to respective electrical signals by the questionnaire component. At 506, the method may include transmitting the respective electrical signals indicating the habits, behaviors, stress and overall well-being of the more than one athlete to the interpreting component connected to the questionnaire component.

In some embodiments, at 508, the method may include receiving the respective electrical signals indicating the habits, behaviors, stress and overall well-being of the more than one athlete by the interpreting component and determining the respective psychological states of the more than one athlete. At 510, the method may include generating state electrical signals indicating a corresponding psychological state of each individual athlete by the interpreting component.

In some embodiments, at 512, the method may include receiving the state electrical signals from the interpreting component for each individual athlete by an aggregating component connected to the interpreting component. At 514, the method may include processing the state electrical signals corresponding to each individual athlete by the aggregating component, generating a group electrical signal indicating the psychological state of the more than one athlete as a group by the aggregating component.

FIG. 5B is a flowchart further illustrating the method from FIG. 5A, in which at 516, the method may include receiving the group electrical signal from the aggregating component by a second display screen. At 518, the method may include transforming the group electrical signal from the aggregating component to a view indicating the psychological state of the more than one athlete as a group by the second display screen.

Figure 6:
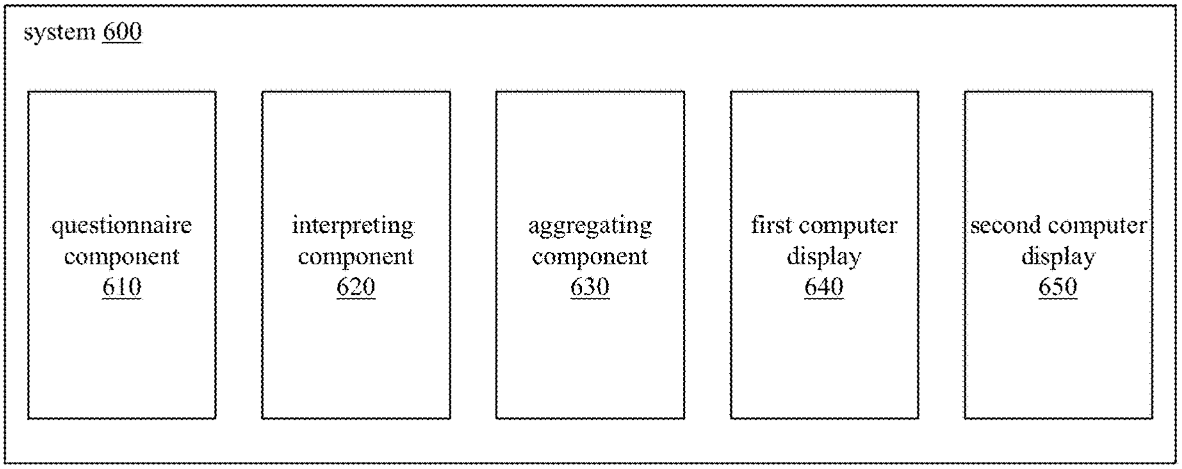
FIG. 6 is a block diagram illustrating a system, in accordance with some embodiments.

FIG. 6 is a block diagram that describes a system 600, according to some embodiments of the present disclosure. In some embodiments, the system 600 may include an aggregating component 630. The system 600 may also include a questionnaire component 610 configured to obtain information regarding habits, behaviors, stress, and overall well-being of one or more athletes and convert the information into one or more electrical signals. The system 600 may also include an interpreting component 620 connected to the questionnaire component 610. In some embodiments, the system 600 may also include a first display screen 640 connected to the aggregating component 630, configured to receive the first electrical signals and display views indicating psychological states of individual athletes. The system 600 may also include a second display screen 650 connected to the aggregating component 630, configured to receive the second electrical signal and display a view indicating the psychological state of the athletes as a group.

In some embodiments, the system is configured to receive the one or more electrical signals from the questionnaire component 610. The system is configured to determine psychological states of the one or more athletes, based on the one or more electrical signals from the questionnaire component 610. The system is configured to convert the determined psychological states into state electrical signals, each corresponding to an individual athlete's psychological state. The system is configured to receive the state electrical signals. The system is configured to process the state electrical signals to generate a group electrical signal indicating the psychological state of the athletes as a group. The system is configured to transform the state electrical signals into first electrical signals and the group electrical signal into a second electrical signal.

In some embodiments, the questionnaire component 610 may also include means for identifying inputs such as habits, behaviors, stress, and well-being metrics of the athletes. In some embodiments, the interpreting component 620 may also include a processor configured to analyze the one or more electrical signals to identify emotional, mental, and physical health indicators. In some embodiments, the aggregating component 630 may be further configured to identify athletes requiring immediate attention based on threshold conditions and generate alerts.

In some embodiments, the aggregating component 630 may be further configured to transform psychological state data into gamified representations displayed on the first and second display screens. In some embodiments, the first and second display screens may be provided by a smart device, tablet, or laptop computer. In some embodiments, the questionnaire component 610 may include an interface for real-time updates and feedback.

In some embodiments, the system 600 may include a communication interface configured to enable video and chat. In some embodiments, the aggregating component 630 may be further configured to assign different flag colors based on well-being thresholds and display corresponding flags on the second display screen 650. In some embodiments, the first display screen 640 may provide a self-care game plan with one or more gamified microlearning processors and at least one wellness exercise.

In some embodiments, the second display screen 650 may display a timeline of one or more psychological states and wellness metrics over a predefined period. In some embodiments, the aggregating component 630 may include a machine learning algorithm to predict future psychological states and provide proactive recommendations for well-being management. In some embodiments, the system 600 may include one or more sensors to measure electrical signals from brain activity in combination with the electrical signals from the questionnaire component 610 to determine a psychological state of the one or more athletes.

Figure 7:
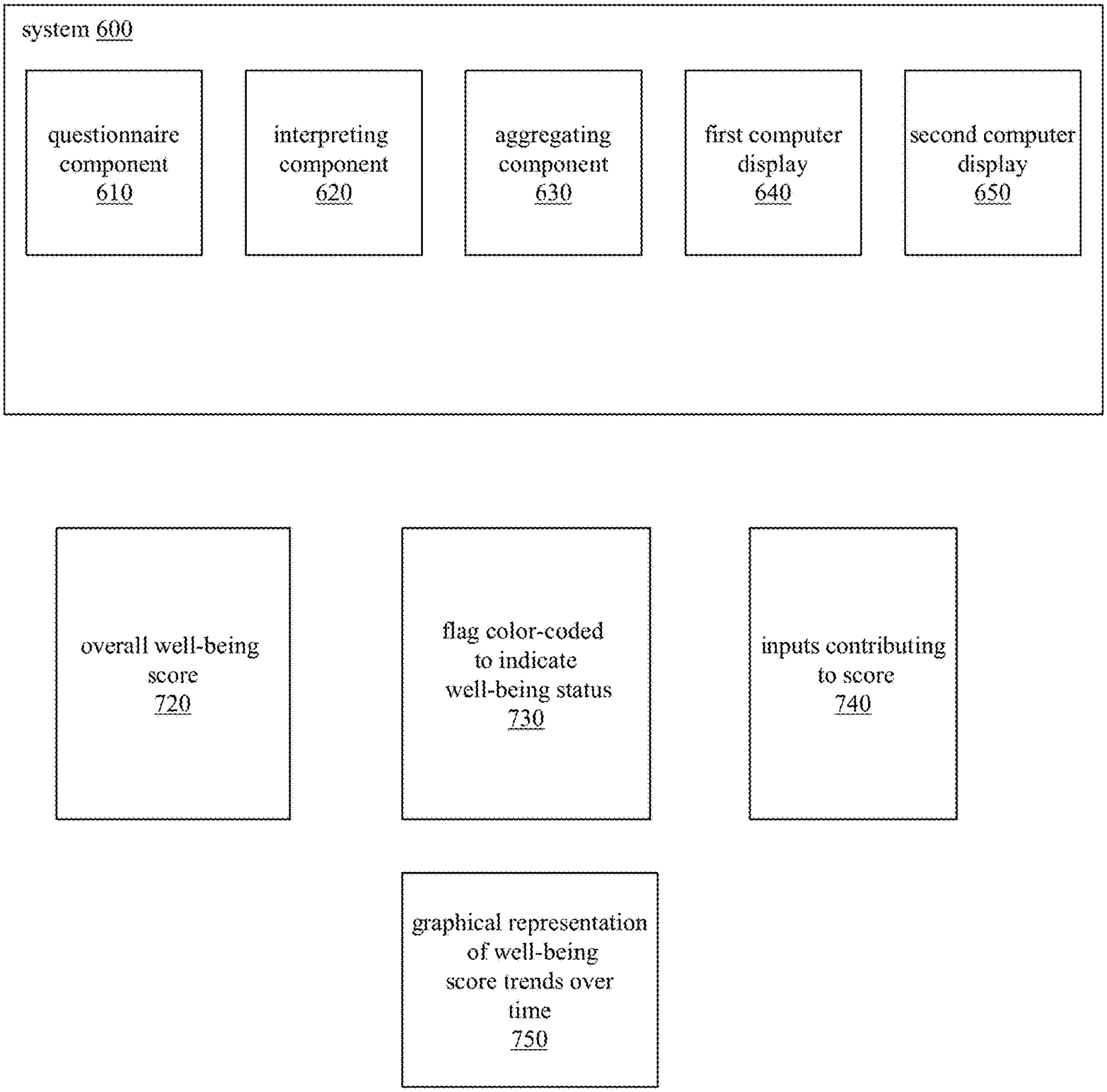
FIG. 7 is a block diagram further illustrating the system from FIG. 6, according to some embodiments of the present disclosure.

FIG. 7 is a block diagram that further describes the system 600 from FIG. 6 configured for processing and displaying well-being metrics. The system comprises several functional components: a questionnaire component 610 for collecting input data from users, an interpreting component 620 that processes and assigns meaning to the collected data, and an aggregating component 630 that consolidates the processed data into a single overall well-being score. The results are displayed on a first display screen 640 and optionally on a second display 650, which may serve different stakeholders or provide additional data visualization.

The output includes an overall well-being score 720, which quantifies the user's state on a scale from 0 to 100. This score is accompanied by a color-coded flag 730, visually indicating the user's well-being status (e.g., green for satisfactory or red for poor). The system also details the number of inputs 740 contributing to the score and the range of dates these inputs represent. Additionally, the system generates a graphical representation 750 of the well-being score over time, highlighting trends and individual input values with their corresponding dates, enabling longitudinal analysis of the user's well-being.

Figure 8:
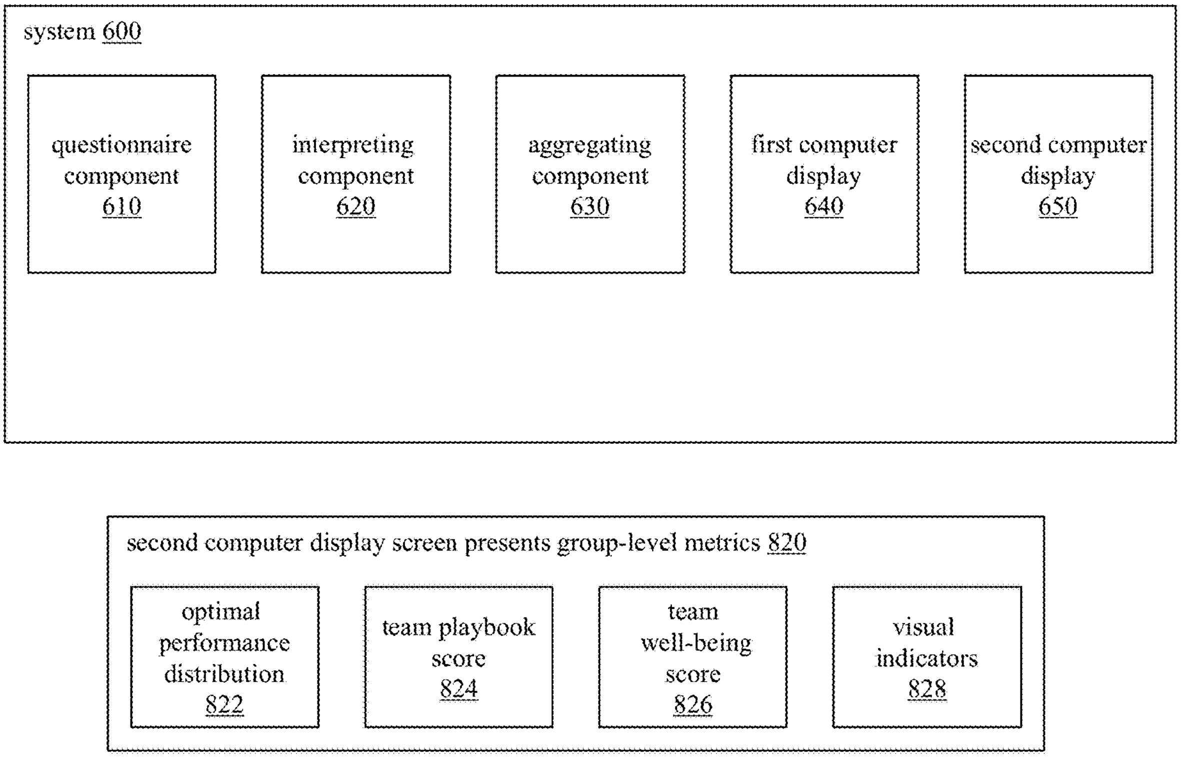
FIG. 8 is a block diagram further illustrating the system from FIG. 6, according to some embodiments of the present disclosure.

FIG. 8 is a block diagram that further describes the system 600 from FIG. 6, according to some embodiments of the present disclosure. In some embodiments, the second display screen presents group-level metrics 820 may include an optimal performance distribution 822, a team playbook performance score 824, a team well-being score 826, and visual indicators 828 of team members requiring wellness checks. In particular, a focus on group-level metrics is displayed on the second display 650. The system retains its core components: the questionnaire component 610 for data collection, the interpreting component 620 for processing user inputs, and the aggregating component 630 for generating overall metrics. These components feed into displays that are tailored for different stakeholders or levels of analysis.

As noted above, the second display 650 presents group-level metrics 820, which are configured for teams and/or organizations to evaluate collective performance and well-being. This includes the optimal performance distribution 822, which provides insights into how team members' performance aligns with predefined benchmarks or optimal ranges. The team playbook score 824 quantifies adherence to or success with team strategies or operational plans. The team well-being score 826 aggregates individual well-being data to represent the overall state of the group, aiding in monitoring collective health and morale. Additionally, visual indicators 828 are used to enhance comprehension and provide immediate, actionable insights, such as graphical or color-coded representations of team metrics for easier interpretation. This configuration supports both individual and collective assessments, enabling comprehensive performance and well-being tracking.

Figure 9:
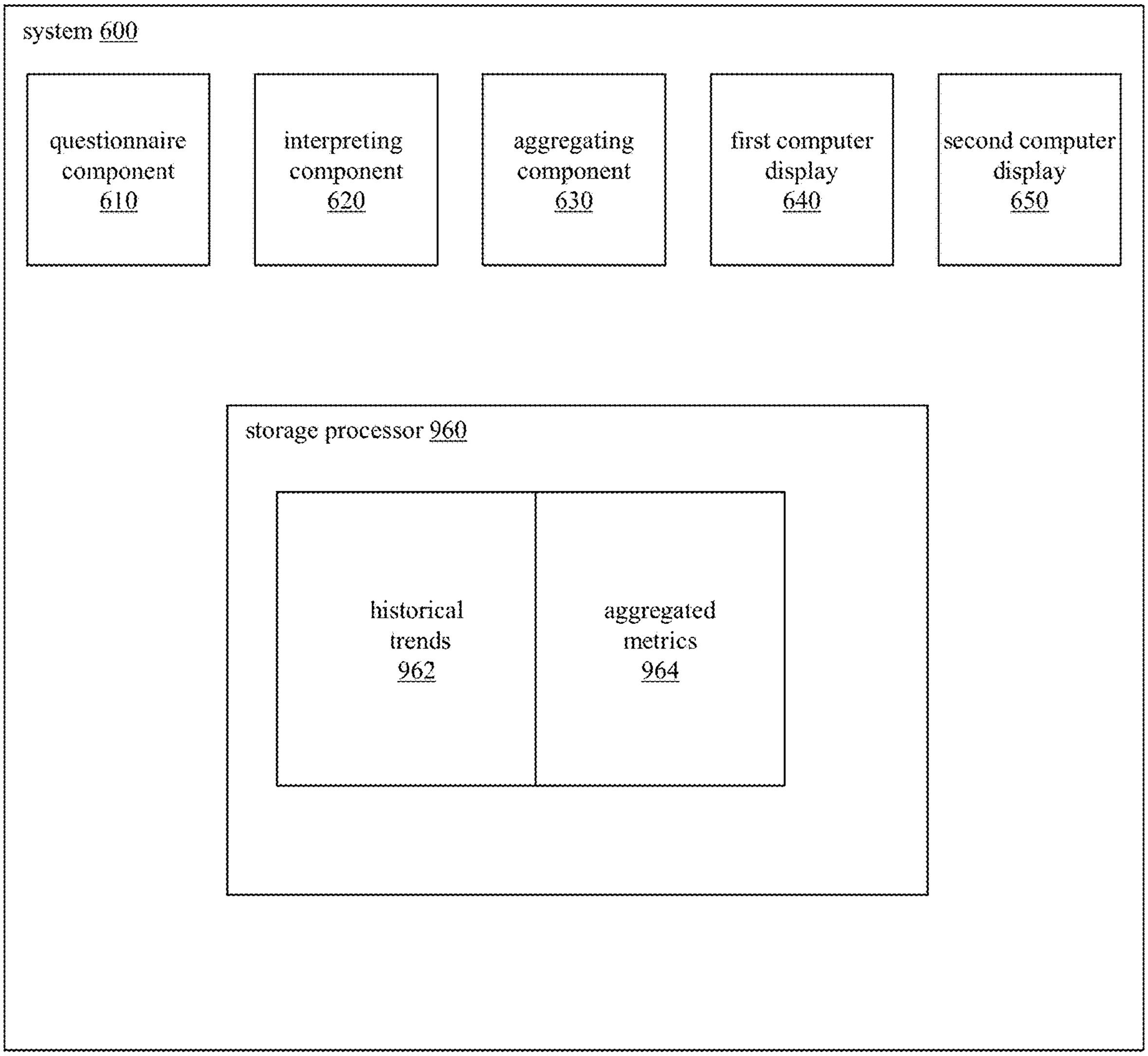
FIG. 9 is a block diagram further illustrating the system from FIG. 6, according to some embodiments of the present disclosure.

FIG. 9 is a block diagram that further describes the system 600 from FIG. 6, according to some embodiments of the present disclosure. In some embodiments, the system 600 may include a storage processor 960 for archiving athlete data. The storage processor 960 may include historical trends 962 and aggregated metrics 964.

Computer Program Products, Methods, and Computing Entities

Various embodiments of the system may be implemented in multiple ways, including as computer program products comprising articles of manufacture. Such computer program products may encompass one or more software components, such as software objects, methods, data structures, and similar constructs. These software components may be developed in a variety of programming languages. For instance, a programming language could be a low-level language, such as assembly language, specific to a particular hardware architecture or operating system platform. Assembly language instructions may require translation into executable machine code via an assembler before execution by the hardware or platform. Alternatively, software components could be coded in high-level programming languages that are portable across different architectures. In such cases, instructions may need conversion to an intermediate form through an interpreter or compiler before execution.

Other examples of programming languages include, but are not limited to, macro languages, shell or command languages, job control languages, scripting languages, database query languages, and report writing languages. In certain embodiments, a software component containing instructions in these languages may execute directly within an operating system or other software environment without additional transformation. Software components may be stored as files or other constructs, and those with similar functionality may be grouped together, such as in specific directories, folders, or libraries. These components may be static (predefined and unchanging) or dynamic (created or modified during execution).

A computer program product may include a non-transitory computer-readable storage medium containing applications, programs, processors, scripts, source code, program code, object code, bytecode, compiled code, interpreted code, machine code, executable instructions, and related elements (collectively referred to here as executable instructions or similar terms). Non-transitory computer-readable storage media include both volatile and non-volatile types.

Examples of non-volatile computer-readable storage media include floppy disks, hard drives, solid-state storage (e.g., SSDs, SSCs, SSMs, enterprise flash drives), magnetic tapes, and optical media such as CDs, DVDs, and Blu-ray discs. Additional examples include ROM, PROM, EPROM, EEPROM, flash memory, memory cards (e.g., MMC, SD, SmartMedia, CompactFlash, Memory Sticks), and advanced memory technologies such as CBRAM, PRAM, FeRAM, NVRAM, MRAM, RRAM, SONOS, FJG RAM, Millipede memory, and racetrack memory.

Volatile computer-readable storage media may include RAM, DRAM, SRAM, FPM DRAM, EDO DRAM, SDRAM, DDR SDRAM (and subsequent DDR generations), RDRAM, TTRAM, T-RAM, Z-RAM, RIMM, DIMM, SIMM, VRAM, cache memory, flash memory, register memory, and similar constructs. It is understood that when a computer-readable storage medium is specified, alternative or additional types of storage media may also be used.

The system may also be implemented as methods, apparatus, systems, computing devices, or other entities. Thus, embodiments may take the form of data structures, hardware systems, or combinations of hardware and software executing instructions stored on a computer-readable medium to perform specific tasks. In some implementations, the system may be realized entirely in hardware, entirely in software, or as a combination of the two.

The embodiments of the system described herein are further illustrated using block diagrams and flowcharts. Each block or step in these illustrations may correspond to a computer program product, a hardware embodiment, or a combination of both. These blocks represent instructions, operations, or steps stored on a computer-readable medium and executed by a computing entity. For example, instructions may be retrieved, loaded, and executed sequentially (one at a time) or in parallel (multiple instructions simultaneously). This flexibility allows the creation of specifically-configured machines capable of performing the operations outlined in the diagrams and illustrations. Therefore, these visual representations encompass various configurations for executing the specified operations, instructions, or steps effectively.

In the sports mental health fitness tracker system, conversions and calculations employ transforming raw data from athletes into actionable insights. When athletes fill out a questionnaire on their sleep quality, stress levels, and emotional well-being, their responses are converted into numerical scores. For example, a sleep quality score might range from 1 (very poor) to 5 (excellent), while stress levels might range from 1 (not stressed) to 5 (extremely stressed). These numerical scores are then converted into electrical signals, with each value corresponding to a specific signal strength, such as 1 representing a low signal strength and 5 representing a high signal strength.

The system then interprets these individual signals to assess the athlete's psychological state. For instance, if an athlete reports a poor sleep quality score of 2, high stress level of 4, and an average emotional well-being score of 3, the system may classify the athlete as experiencing a high stress state. This is calculated by assigning weights to each component based on its importance, such as a weight of 0.3 for sleep, 0.4 for stress, and 0.3 for well-being, and calculating a weighted average score. In this case, the system calculates a score of 3.1, which would correspond to a high stress signal. This score is then converted into an electrical signal that reflects the athlete's mental state.

If multiple athletes are involved, the system aggregates their individual state signals to calculate a group-level signal. For example, if Athlete 1 has a high stress signal of 3.1, Athlete 2 has a moderate stress signal of 2.5, and Athlete 3 has a low stress signal of 1.8, the system calculates an average signal of 2.47, which represents the overall psychological state of the group. This average signal is then converted into an electrical signal, which can be used to trigger visual or audio feedback on a display. The processed electrical signals are then converted into user-friendly display outputs. On the first screen, individual athlete data might be shown as a well-being score from 0 to 100, accompanied by a color-coded flag system where red indicates high stress, yellow indicates moderate stress, and green indicates low stress. A graph might also show an athlete's well-being score over time. On the second screen, the group signal might display the team's collective mental health status, including performance metrics like a team wellness score and a schedule for wellness checks. This comprehensive process of conversions and calculations allows the system to provide coaches and trainers with valuable insights into the mental health of athletes, both individually and as a team.

As noted above, the conversion of a signal into an electrical signal involves several steps, turning data into a format that can be processed by the system's hardware and displayed on screens. First, the data from the athlete's responses to the questionnaire (such as their sleep quality, stress level, or emotional well-being) is collected. Each response is quantified, usually with a numerical value-like a score from 1 to 5 for each category. For instance, a sleep score of 3 (on a scale from 1 to 5) might correspond to a moderate level of sleep quality, and a stress score of 4 might indicate high stress. Next, this numerical data is translated into an electrical signal, which is essentially a representation of the data in a form that can be processed by electronic systems. This conversion process involves encoding the data as voltage or current levels. For example, a value of 1 might correspond to a low voltage (say, 1 volt), and a value of 5 might correspond to a higher voltage (such as 5 volts). The greater the score (such as a 5 for stress), the stronger the electrical signal generated. The electrical signal is then sent to the interpreting component of the system. Here, it might be amplified or modified, depending on the system's requirements, to produce a signal suitable for further processing. The signal is typically in the form of a direct current (DC) voltage, which is easy for computers and displays to interpret and use.

Once the signal is processed and interpreted, it can be used to trigger specific outputs, such as a visual display on a screen, based on the athlete's condition. For example, a high stress level might result in a red flag on the display, or a graph showing a decline in well-being might be generated to indicate a need for intervention. In essence, the process of converting a questionnaire response into an electrical signal involves transforming subjective data into a standardized, measurable format that can be represented electronically. This conversion enables the system to analyze, aggregate, and display the data, providing actionable insights into the athlete's well-being.

In an embodiment, The Playbook application may implement a technical solution to monitoring and enhancing mental health for athletes and teams. By tracking stress, well-being, and resilience, it provides athletes with actionable, data-driven insights to improve performance while equipping teams with tools to proactively prevent crises. The application functions as both a mental health performance monitor and a proactive crisis prevention tool. When assessments reveal that a player has entered an unhealthy range, referred to as the "Red Zone," they are immediately connected to tailored mental health resources for support, both within and outside the team environment.

The Playbook application emphasizes long-term mental health management by offering gamified assessments that produce scores ranging from 0 to 100. These assessments measure stress, well-being, and resilience, forming an overall Playbook Performance Score akin to a batting average. The app tracks mental health trends over weeks, months, and years, ensuring users can monitor their progress and stay engaged over time. Athlete users, the primary audience, can view personal metrics, complete daily and periodic assessments, track trends, and access resources tailored to their needs. Additionally, quick daily check-ins allow athletes to log their mood, contributing to the team's overall mental health trends. For those in the "Red Zone," the app directs users to immediate support while notifying team administrators for further action.

Admin users, such as mental health professionals, athletic trainers, and coaches, use the Playbook's web-based dashboard to manage team profiles, monitor athlete metrics, and receive alerts when intervention is required. They can perform assessments, access tailored resources for their athletes, and take proactive steps to prevent crises. Staff users, with more limited permissions, can view team stats and engage with their assessments and resources. The app ensures HIPAA compliance, maintaining athlete privacy while providing secure visibility for trusted care teams.

Core features of the Playbook application include gamified assessments, real-time insights, customizable action plans, and HIPAA-compliant data security. Assessments are grounded in standardized psychological tools, measuring stress, well-being, and resilience. Each assessment takes less than five minutes to complete, and results are presented using a color-coded system—Green (healthy), Yellow (needs improvement), and Red (unhealthy). The Playbook Performance Score aggregates these metrics to provide a snapshot of an athlete's overall mental health. Consistent use improves the app's ability to track and predict trends, offering a meaningful picture of mental health over time.

Athletes and administrators can easily access actionable insights and resources through various features, such as the "Today's Check-In" section for daily mood tracking and the "View Mood Trends" button for weekly and monthly patterns. If an athlete enters the "Red Zone," coaches and administrators are alerted and guided through the Red Zone Action Plan. This plan includes steps for rapid assessment, connecting athletes to appropriate care, and ensuring follow-up actions are completed. Recommendations may involve referring the athlete to a team clinician, a local provider, or emergency services. The Playbook's privacy protocols ensure that athletes always know who has access to their scores and can withdraw consent if needed.

The Playbook application also supports team administrators in managing their teams through features like the Team Administration dashboard, which allows users to add, edit, and manage team profiles, contacts, and resources. Admins can designate team members as contacts for support and share information about local resources such as mental health clinics and emergency services. The application also allows for customization of team details, including logos and playlists, to enhance engagement. In summary, the Playbook app combines robust mental health monitoring with a proactive approach to crisis prevention, offering athletes and teams the tools they need to build resilience, enhance performance, and maintain well-being over the long term. Through its gamified assessments, actionable insights, and privacy-first design, the application establishes itself as an essential tool for modern athletic teams.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A system for measuring mental health and overall well-being of an athlete comprising:

a questionnaire component for obtaining data based on one or more habits, behaviors, stress, or overall well-being of the athlete, wherein the questionnaire component converts the data to an electrical signal encoded as voltage or current levels indicating the habits, behaviors, stress, or overall well-being of the athlete;

an interpreting component connected to the questionnaire component;

wherein the interpreting component receives the electrical signal indicating the habits, behaviors, stress and overall well-being of the athlete from the questionnaire component and determines a psychological state of the athlete, based on a strength of the electrical signal, wherein the interpreting component changes a determination of the psychological state of the athlete to state electrical signals as direct current (DC) voltage indicating the psychological states of the athlete;

an aggregating component connected to the interpreting component, the aggregating component receiving the state electrical signals from the interpreting component for the athlete, the aggregating component processing the state electrical signals corresponding to the athlete to generate a group electrical signal indicating the psychological state of the more than one athlete as a group; and wherein the aggregating component transforms each state electrical signal of the state electrical signals to a respective first electrical signal, wherein the aggregating component transforms the group electrical signal into a second electrical signal;

the interpreting component to apply one or more algorithms to analyze the electric signals and determine a first electrical signal indicating the psychological state of the athlete; and a first display screen of an electronic device connected to the interpreting component, the first display screen to display the first electrical signal from the interpreting component, the first display screen to transform the first electrical signal from the interpreting component to a view to indicate the psychological state of the athlete on the first display screen;

conductive electrodes;

one or more physiological sensors use the conductive electrodes configured to measure raw electrical signals from a body of the athlete in combination with the electrical signal from the questionnaire component to determine a psychological state of the athlete;

a microcontroller integrated onto a processor of the one or more sensors to filter noise, using a digital filter, from the raw electrical signals;

a sensor interface comprising the one or more physiological sensors, wherein the sensor interface transmits the psychological state of the athlete to the interpreting component;

a processor configured to integrate and analyze the electrical signals from the questionnaire component and the sensor interface using one or more machine learning models, the machine learning models trained to identify psychological states including burnout, anxiety, and resilience;

a model evaluation pipeline executed by the processor, the model evaluation pipeline configured to perform cross-validation on the one or more machine learning models, measure model performance using precision, recall, and F1 score metrics, detect misclassification of the psychological states, and iteratively fine-tune the one or more machine learning models based on the detected misclassification;

wherein the system generates a composite psychological state signal based on both subjective and physiological inputs and displays a visual representation of the composite signal on the first display screen, including a numerical well-being score and a color-coded flag indicator;

a communication interface to connect the athlete with a mental health professional, based on the numerical well-being score and the color-coded flag indicator, wherein the interpreting component is configured to classify the athlete as experiencing a high stress psychological state, wherein the composite psychological state signal represents the high stress psychological state and is output as a red alert on the communication interface; and one or more gamified microlearning processors are configured to provide a self-care game plan and at least one wellness exercise to the athlete experiencing the high stress psychological state in response to the red alert.

2. The system of claim 1, wherein the system to determine the psychological state of more than one athlete as a group, further comprising a second display screen connected to the aggregating component, the second display screen receiving the group electrical signal from the interpreting component into a second electrical signal, the second display screen transforming the group electrical signal from the aggregating component to a view indicating the psychological state of the more than one athlete as a group on the second display screen.

3. A method for measuring mental health and overall well-being of an athlete comprising:

obtaining information regarding one or more habits, behaviors, stress, or overall well-being of the athlete by a questionnaire component;

changing the information indicating the habits, behaviors, stress and overall well-being of the athlete to an electrical signal by the questionnaire component;

transmitting the electrical signal indicating the habits, behaviors, stress and overall well-being of the athlete to an interpreting component connected to the questionnaire component;

determining a psychological state of the athlete by the interpreting component, the interpreting component changing the determination of the psychological state to a state electrical signal indicating the psychological state of the athlete;

measuring, using one or more physiological sensors electrically connected to one or more conductive electrodes, raw electrical signals from a body of the athlete in combination with the electrical signal from the questionnaire component to generate a composite psychological state of the athlete;

filtering noise, using a microcontroller integrated onto a processor of the one or more sensors using a digital filter, from the raw electrical signals;

executing, using a processor of the interpreting component, one or more machine learning models trained on labeled mental health data to classify the psychological state of the athlete into one or more categories, the processor further configured to analyze time-series trends in historical data to detect deviations over a predefined time window;

a model evaluation pipeline executed by the processor, the model evaluation pipeline configured to perform cross-validation on the one or more machine learning models, measure model performance using precision, recall, and F1 score metrics, detect misclassification of the psychological states, and iteratively fine-tune the one or more machine learning models based on the detected misclassification;

transmitting the state electrical signal from the interpreting component to a first display screen connected to the interpreting component, the first display screen transforming the state electrical signal from the interpreting component to a view indicating the psychological state of the athlete on the first display screen;

trigging, via the interpreting component, an alert to a designated support entity when the time-series trend of psychological state data exceeds a defined threshold indicative of elevated risk;

instructing, based on the alert, that a wellness check be performed on the athlete within 24 hours;

classifying, using the interpreting component, the athlete as experiencing a high stress psychological state, outputting as a red alert on a communication interface when the composite psychological state signal represents the high stress psychological state and; and responsive to the triggering, providing, by the first display screen, a self-care game plan with one or more gamified microlearning processors and at least one wellness exercise to the athlete experiencing the high stress psychological state in response to the red alert.

4. The method of claim 3, and further using the method to measure the mental health and overall well-being of more than one athlete, the method comprising the steps of:

obtaining information regarding the habits, behaviors, stress and overall well-being of the more than one athlete by the questionnaire component;

changing the information indicating the habits, behaviors, stress and overall well-being of the more than one athlete to respective electrical signals by the questionnaire component;

transmitting the respective electrical signals indicating the habits, behaviors, stress and overall well-being of the more than one athlete to the interpreting component connected to the questionnaire component;

receiving the respective electrical signals indicating the habits, behaviors, stress and overall well-being of the more than one athlete by the interpreting component and determining the respective psychological states of the more than one athlete, generating state electrical signals indicating a corresponding psychological state of each individual athlete by the interpreting component;

receiving the state electrical signals from the interpreting component for each individual athlete by an aggregating component connected to the interpreting component; processing the state electrical signals corresponding to each individual athlete by the aggregating component, generating a group electrical signal indicating the psychological state of the more than one athlete as a group by the aggregating component;

receiving the group electrical signal from the aggregating component by a second display screen; and transforming the group electrical signal from the aggregating component to a view indicating the psychological state of the more than one athlete as a group by the second display screen.

5. A system for tracking athlete mental health fitness, comprising:

a questionnaire component configured to obtain information regarding habits, behaviors, stress, and overall well-being of one or more athletes and convert said information into a first electrical signal comprising a set of quantified signal values representing the habits, behaviors, stress, or overall well-being of the athlete;

an interpreting component connected to the questionnaire component, configured to:

receive the first electrical signal from the questionnaire component and extract signal features using one or more signal processing techniques;

determine psychological states of the one or more athletes by applying a machine learning classification model trained on labeled psychological signal information based on a strength of the electrical signal; and convert the determined psychological states into a second electrical signal as direct current (DC) voltage indicating a classified psychological state of the athlete;

an aggregating component connected to the interpreting component configured to:

receive the state electrical signals from the interpreting component for the athlete, process the state electrical signals corresponding to the athlete to generate a group electrical signal indicating the psychological state of the athletes as a group, and transform each state electrical signal of the state electrical signals into first electrical signals and the group electrical signal into a second electrical signal;

a first display screen connected to the aggregating component, configured to receive the first electrical signals and display views indicating psychological states of individual athletes;

a second display screen connected to the aggregating component, configured to receive the second electrical signal and display a view indicating the psychological state of the athletes as a group;

conductive electrodes;

one or more physiological sensors use the conductive electrodes configured to measure raw electrical signals from a body of the athlete in combination with the electrical signal from the questionnaire component to determine a composite psychological state of the athlete;

a microcontroller integrated onto a processor of the one or more sensors to filter noise, using a digital filter, from the raw electrical signals;

a sensor interface transmits the psychological state of the athlete to the interpreting component; and a model evaluation pipeline executed by the processor, the model evaluation pipeline configured to perform cross-validation on the one or more machine learning models, measure model performance using precision, recall, and F1 score metrics, detect misclassification of psychological states, and iteratively fine-tune the one or more machine learning models based on the detected misclassification;

wherein the interpreting component is configured to classify the athlete as experiencing a high stress psychological state, wherein the composite psychological state signal represents the high stress psychological state and is output as a red alert on a communication interface; and one or more gamified microlearning processors are configured to provide a self-care game plan and at least one wellness exercise to the athlete experiencing the high stress psychological state in response to the red alert.

6. The system of claim 5, wherein the questionnaire component further includes means for identifying inputs such as habits, behaviors, stress, and well-being metrics of the athletes.

7. The system of claim 5, wherein the interpreting component includes a processor configured to analyze the one or more electrical signals to identify emotional, mental, and physical health indicators.

8. The system of claim 5, wherein the aggregating component is further configured to identify athletes requiring immediate attention based on threshold conditions and generate alerts.

9. The system of claim 5, wherein the first display screen presents well-being metrics for individual athletes, including:

an overall well-being score;

a flag color-coded to indicate well-being status;

a graphical representation of one or more well-being score trends over time; and a number of inputs contributing to the score.

10. The system of claim 5, wherein the second display screen presents group-level metrics, including:

an optimal performance distribution, a team playbook performance score, a team well-being score, and visual indicators of team members requiring wellness checks.

11. The system of claim 5, wherein the aggregating component is further configured to transform psychological state data into gamified representations displayed on the first and second display screens.

12. The system of claim 5, wherein the first and second display screens are provided by a smart device, tablet, or laptop computer.

13. The system of claim 5, wherein the questionnaire component includes an interface for real-time updates and feedback.

14. The system of claim 5, further comprising:

a communication interface configured to enable video and chat.

15. The system of claim 5, wherein the aggregating component is further configured to assign different flag colors based on well-being thresholds and display corresponding flags on the second display screen.

16. The system of claim 5, wherein the first display screen provides a self-care game plan with one or more gamified microlearning processors and at least one wellness exercise.

17. The system of claim 5, wherein the second display screen displays a timeline of one or more psychological states and wellness metrics over a predefined period.

18. The system of claim 5, further comprising a storage processor for archiving athlete data, including historical trends and aggregated metrics.

19. The system of claim 5, wherein the aggregating component includes a machine learning algorithm to predict future psychological states and provide proactive recommendations for well-being management.

20. The system of claim 5, further comprising one or more sensors to measure electrical signals from brain activity in combination with the electrical signals from the questionnaire component to determine a psychological state of the one or more athletes.

* * * * *